United States Patent [19]

Finger

[11] 4,218,400
[45] Aug. 19, 1980

[54] PROCESS FOR THE PRODUCTION OF FLUORENONE BY CATALYTIC OXIDATION OF FLUORENE

[75] Inventor: Carl Finger, Essen, Fed. Rep. of Germany

[73] Assignee: Rütgerswerke Aktiengesellschaft, Frankfurt am Main, Fed. Rep. of Germany

[21] Appl. No.: 873,755

[22] Filed: Jan. 30, 1978

[30] Foreign Application Priority Data

Feb. 4, 1977 [DE] Fed. Rep. of Germany ....... 2704648

[51] Int. Cl.² .............................................. C07C 45/02
[52] U.S. Cl. ................................................... 568/321
[58] Field of Search ................................. 260/590 FA

[56] References Cited

U.S. PATENT DOCUMENTS 3,855,252  12/1974  Robinson et al. ............. 260/590 FB
3,875,237  4/1975   Niznik ........................... 260/590 FB

FOREIGN PATENT DOCUMENTS 1227144  4/1971  United Kingdom .................. 260/340.2

OTHER PUBLICATIONS

Sprinzak, J.A.C.S., vol. 80, pp. 5449-5454 (1958).
Alneri et al., Tet. Lett. (#24), pp. 2117-2118 (1977).

Primary Examiner—Bernard Helfin
Assistant Examiner—James H. Reamer
Attorney, Agent, or Firm—Beveridge, DeGrandi, Kline & Lunsford

[57] ABSTRACT

An improved process for the production of pure fluorenone by oxidation of fluorene with air or oxygen at ambient temperature in the presence of a quaternary salt, the improvement comprising carrying out the reaction in a suspension of fluorene or a fluorene-containing fraction in an aprotic immiscible with water solvent, such as a α-methyl naphthalene, which contains and is primed with a 30%–60% aqueous alkali metal hydroxide solution, and intimately mixing the organic and aqueous phases during the reaction.

8 Claims, No Drawings

PROCESS FOR THE PRODUCTION OF FLUORENONE BY CATALYTIC OXIDATION OF FLUORENE

BACKGROUND OF THE INVENTION

1. Field of the Invention

The present invention relates to a process for the production of pure fluorenone by oxidation of fluorene fractions with air or oxygen in the presence of quaternary salts.

2. Description of the Prior Art

According to K. Kinoshita, K. Okada and S. Hashimoto, Nippon Kagaku Zasshi 80, 206-8 (1959), it has been known to produce fluorenone in the liquid phase by air oxidation from fluorene in pyridine as a solvent and sodium hydroxide at about 95° C. However, the process requires a cumbersome processing (working up) of the alkaline solution by treatment with acids and subsequent extraction with ether for obtaining the fluorenone. The yield is at most 50%.

In British Pat. No. 834,590, it has been proposed to oxidize fluorenone by oxidation of fluorene in propionic acid in the presence of cobalt bromide by passing over oxygen. The yield of fluorenone is given at 75%.

According to Y. Sprinzak, J. Am. Chem. Soc. 80, 5449-55 (1958), it has been known to treat fluorene in a pyridine solution in the presence of Triton B as catalyst with oxygen. However, production on an industrial scale would be uprofitable because of the required processing of the reaction product connected with large quantities of liquid for the isolation of the fluorenone as well as because of the consumption of fairly large quantities of pyridine.

German Pat. No. 1,262,268 teaches the production of fluorenone by catalytic oxidation of molten fluorene at an elevated temperature of about 150° C. in the presence of stearates or resinates of manganese, cobalt and lead. This process requires special catalysts as well as the traditional measure of melting the fluorene. Moreover the yields, which do not exceed 50%, are not satisfactory.

According to T. Soboleva and V. A. Proskuryakow Zh. Prikl. Khm. (Leningrad) 1970, 43(8), it has furthermore been taught to obtain fluorenone by air oxidation of a fluorene emulsion in aqueous alkali at 175° C. under pressure. However, this process requires a higher expenditure of power than is desirable.

Finally, it has also been taught in German published application No. 1,940,051 (priority of Aug. 6, 1969) to oxidize fluoren through the oxidation of fluorene in acetic acid in the presence of cobalt and manganese acetates as well as potassium bromide by passing over air. In this process too, the yields amount to only about 50%.

It is therefore a primary object of the present invention to provide a process for the production of pure fluorenone which is equally advantageous from both industrial and economic standpoints.

SUMMARY OF THE INVENTION

It has been found that the above object can be attained by an improved process for the production of pure fluorenone by oxidation of fluorene with air or oxygen at normal or ambient temperature with the use of a quaternary salt. The improvement comprises carrying out the reaction in a suspension of fluorene or of a fluorene-containing fraction in an aprotic organic solvent immiscible with water, which contains and is primed with an aqueous alkali metal hydroxide solution containing from 30% to 60% by weight of the alkali metal hydroxide, and by intimately mixing the organic and aqueous phases during the reaction.

DESCRIPTION OF THE PREFERRED EMBODIMENTS

The quaternary salt used is preferably a quaternary ammonium salt such as benzyl-trimethyl-ammonium hydroxide which is available commercially as Triton B, although other quaternary salts such as the quaternary phosphonium salts may be used.

All of the alkali metal hydroxides can be used. The preferred alkali metal hydroxide is sodium hydroxide which is preferably used in a 40% by weight aqueous solution.

Contrary to the previously known processes, the fluorene oxidation according to the process of the present invention will succeed with very high yields of about 90% with industrially simple means under atmospheric pressure. Beyond that, the present process is not comparable with those described above since it takes place in a two-phase system. This is also the case according to the Soboleva et al. process previously cited, but there the use of pressure is required. Hitherto the production was limited to processes in which only aprotic solvents miscible with water such as, for example, pyridine, could be used. The process of the present invention shows that the oxidation is also possible in a suspension of aprotic, solvents immiscible with water, such as for example, methyl naphthalene. The simultaneous advantage is the saving of solvent which is required in the process of the present invention only in an approximate ratio of 1:1 to the tar component. In the case of the use of pyridine, on the other hand, higher portions of solvents are necessary. Thus, Y. Sprinzak, J. Am. Chem. Soc. 80, 5449-55 (1958) prescribes (page 5453) that 10 ml. of pyridine are required per 0.01 mole of fluorene.

As a result of the two-phase system used in the present invention, it is possible after completion of the oxidation process to separate the homogeneous organic phase from the inorganic aqueous phase, that is to say, from the alkali metal hydroxide solution. Since the solvents such as methyl-naphthalene do not dissolve in water, a mixing of the two phases will be avoided. The ratio of organic phase to alkali solution phase is not critical and may generally be from 2:1 to 10:1.

It is therefore possible within the scope of the process of the present invention to distill the fluorenone off directly without further processing of the reaction mixture after the separation of the phases. With the distillation as the final step, there is the advantage that it is not absolutely necessary to use pure fluorene for the oxidation, but that one may oxidize corresponding fluorene cuts as obtained in the case of tar processing (cf. Example 6).

The concentration of the alkali metal hydroxide solution should only be such so as to assure that the concentration which is reduced during the reaction is not substantially below 30% by weight at the end of the reaction. In Example 1 to follow, in which a 40% sodium hydroxide solution was used, the decanted sodium hydroxide solution had a content of about 34% of alkali and after concentration may be used for a new oxidation batch. The methyl naphthalene distilled off may likewise be used for a new oxidation batch. The process also permits the use of fluorene fractions with a fluorene content of 50%–75% fluorene.

The following non-limiting examples will illustrate the possibilities of the use of various starting products for carrying out the oxidation process of the invention.

EXAMPLE 1

In a vessel with a stirrer mechanism, 1 kg. of pure fluorene (95–97%) was suspended in 1 kg. α-methyl naphthalene, primed with 300 g. of a 40% sodium hydroxide solution. Then 1 g. of Triton B (benzyl-trimethyl-ammonium hydroxide) was added and air was conducted through the suspension at 20°–30° C. while stirring vigorously. After each 10 hours another gram of Triton B was added. After a reaction time of 48 hours, the stirrer mechanism was stopped. The product was allowed to settle and then the homogeneous, organic phase was separated from the inorganic phase. From the organic phase, the methyl naphthalene was first distilled over by helm distillation and subsequently the fluorenone (95%) was distilled over at standard pressure or under vacuum through a short Vigreux column. The yield of fluorenone (95%) amounted to 986 g.=91% of theory.

EXAMPLE 2

The operation was conducted under the same conditions and with the same quantitative ratios as stated in Example 1; however, the α-methyl naphthalene was replaced by a commercial methyl naphthalene fraction which had a content of 15–30% α-methyl naphthalene, 45–60% β-methyl naphthalene as well as a residue of quinoline bases and boiling attendant. The yield of fluorenone (95%) amounted to 960 g.=88% of theory.

EXAMPLE 3

The operation was conducted under the same conditions and with the same quantitative ratios as stated in Example 1; however, the α-methyl naphthalene was replaced by a de-based commercial methyl naphthalene fraction. The yield of fluorenone (95%) amounted to 972 g.=90% of theory.

EXAMPLE 4

The operation was conducted under the same conditions and with the same quantitative ratios as stated in Example 1 with the exceptions that instead of pure fluorene, a commercial fluorene fraction with a fluorene content of at least 50% was used and that the α-methyl naphthalene was replaced by pure quinoline. The yield of fluorenone (95%) amounted to 1.035 g.=96% of theory.

EXAMPLE 5

Again, the operation was conducted under the same conditions and with the same quantitative ratios as stated in Example 1 with the exceptions that instead of pure fluorene, a commercial fluorene fraction with a fluorene content of at least 50% was used and that the α-methyl naphthalene was replaced by a raw quinoline fraction. The yield of fluorenone (95%) amounted to 1.016 kg.=94% of theory.

EXAMPLE 6

The operation was conducted under the same conditions and with the same quantitative ratios as stated in Example 1, with the exceptions that instead of pure fluorene, a commercial fluorene fraction with a fluorene content of 72% was used and as a suspension agent, α-methyl naphthalene was used. The distillation was conducted with the aid of a 28-tray column under vacuum at a pressure of 150 or 50 mm of mercury. The yield of fluorenone (95%) amounted to 652 g.=85% of theory.

What is claimed is:

1. In a process for the production of pure flourenone by oxidation of flourene with air or oxygen at ambient temperature in the presence of a quanternary salt, the improvement which comprises carrying out the reaction in a suspension of flourene or a flourene-containing fraction in an aprotic water immiscible solvent which is primed with an aqueous solution containing 40% by weight of sodium hydroxide, intimately mixing the organic and aqueous phases during the reaction and separating the pure flourenone from the reaction mixture.

2. The process according to claim 1 wherein the, solvent is α-methyl naphthalene, quinoline or commercial fractions of these solvents.

3. The process according to claim 1 wherein a fluorene-containing fraction with a fluorene content of at least 50% by weight is used.

4. The process according to claim 3 wherein the fluorene-containing fraction has a fluorene content of from 50% to 75% by weight fluorene.

5. The process according to claim 1 wherein the solvent is α-methyl naphthalene, quinoline or commercial fractions of these solvents.

6. The process according to claim 1 wherein a fluorene-containing fraction with a fluorene content of at least 50% by weight is used.

7. The process according to claim 6 wherein the fluorene-containing fraction has a fluorene content of from 50% to 75% by weight fluorene.

8. The process according to claim 1 wherein after the reaction, the organic phase is separated from the aqueous phase and the pure fluorenone is distilled from said separated organic phase.

* * * * *